(12) United States Patent
Estrada et al.

(10) Patent No.: US 8,026,279 B2
(45) Date of Patent: Sep. 27, 2011

(54) CRYSTALLINE FORM OF γ-AMINOBUTYRIC ACID ANALOG

(75) Inventors: Tono Estrada, Santa Clara, CA (US); Stephen P. Raillard, Mountain View, CA (US)

(73) Assignee: XenoPort, Inc., Santa Clara, CA (US)

( * ) Notice: Subject to any disclaimer, the term of this patent is extended or adjusted under 35 U.S.C. 154(b) by 757 days.

(21) Appl. No.: 10/966,507

(22) Filed: Oct. 14, 2004

(65) Prior Publication Data

US 2005/0154057 A1    Jul. 14, 2005

Related U.S. Application Data

(60) Provisional application No. 60/511,287, filed on Oct. 14, 2003.

(51) Int. Cl.
| | |
|---|---|
| *A61K 31/24* | (2006.01) |
| *A61K 31/22* | (2006.01) |
| *C07C 61/00* | (2006.01) |
| *C07C 205/00* | (2006.01) |

(52) U.S. Cl. ......... 514/534; 514/546; 562/509; 560/125

(58) Field of Classification Search .................. 560/250, 560/125; 514/534, 546; 562/250, 509
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,024,175 A | 5/1977 | Satzinger et al. | |
| 4,087,544 A | 5/1978 | Satzinger et al. | |
| 5,084,169 A | 1/1992 | Noble et al. | |
| 5,112,598 A | 5/1992 | Biesalski | |
| 5,556,611 A | 9/1996 | Biesalski | |
| 5,563,175 A | 10/1996 | Silverman et al. | |
| 5,698,155 A | 12/1997 | Grosswald et al. | |
| 6,001,876 A | 12/1999 | Singh | |
| 6,020,370 A | 2/2000 | Horwell et al. | |
| 6,028,214 A | 2/2000 | Silverman et al. | |
| 6,054,482 A | 4/2000 | Augart et al. | |
| 6,103,932 A | 8/2000 | Horwell et al. | |
| 6,117,906 A | 9/2000 | Silverman et al. | |
| 6,310,098 B1 | 10/2001 | Guttuso, Jr. | |
| 6,816,787 B2 | 11/2004 | Gallop et al. | |
| 6,833,140 B2 | 12/2004 | Cundy et al. | |
| 6,927,036 B2 | 8/2005 | Gallop et al. | |
| 6,992,109 B1 | 1/2006 | Segal et al. | |
| 7,144,882 B2 | 12/2006 | Coe et al. | |
| 7,186,855 B2 | 3/2007 | Gallop et al. | |
| 7,227,028 B2 | 6/2007 | Gallop et al. | |
| 7,232,924 B2 * | 6/2007 | Raillard et al. ............... | 560/115 |
| 7,423,169 B2 | 9/2008 | Raillard et al. | |

(Continued)

FOREIGN PATENT DOCUMENTS

CA    2449729    12/2002

(Continued)

OTHER PUBLICATIONS

U.S. Appl. No. 60/606,637, filed Aug. 13, 2004, Gallop et al.

(Continued)

*Primary Examiner* — Taylor Victor Oh
(74) *Attorney, Agent, or Firm* — Dorsey & Whitney LLP

(57) ABSTRACT

A crystalline form of a γ-aminobutyric acid analog, and methods of preparing same, are provided.

17 Claims, 2 Drawing Sheets

U.S. PATENT DOCUMENTS

Figure 1:
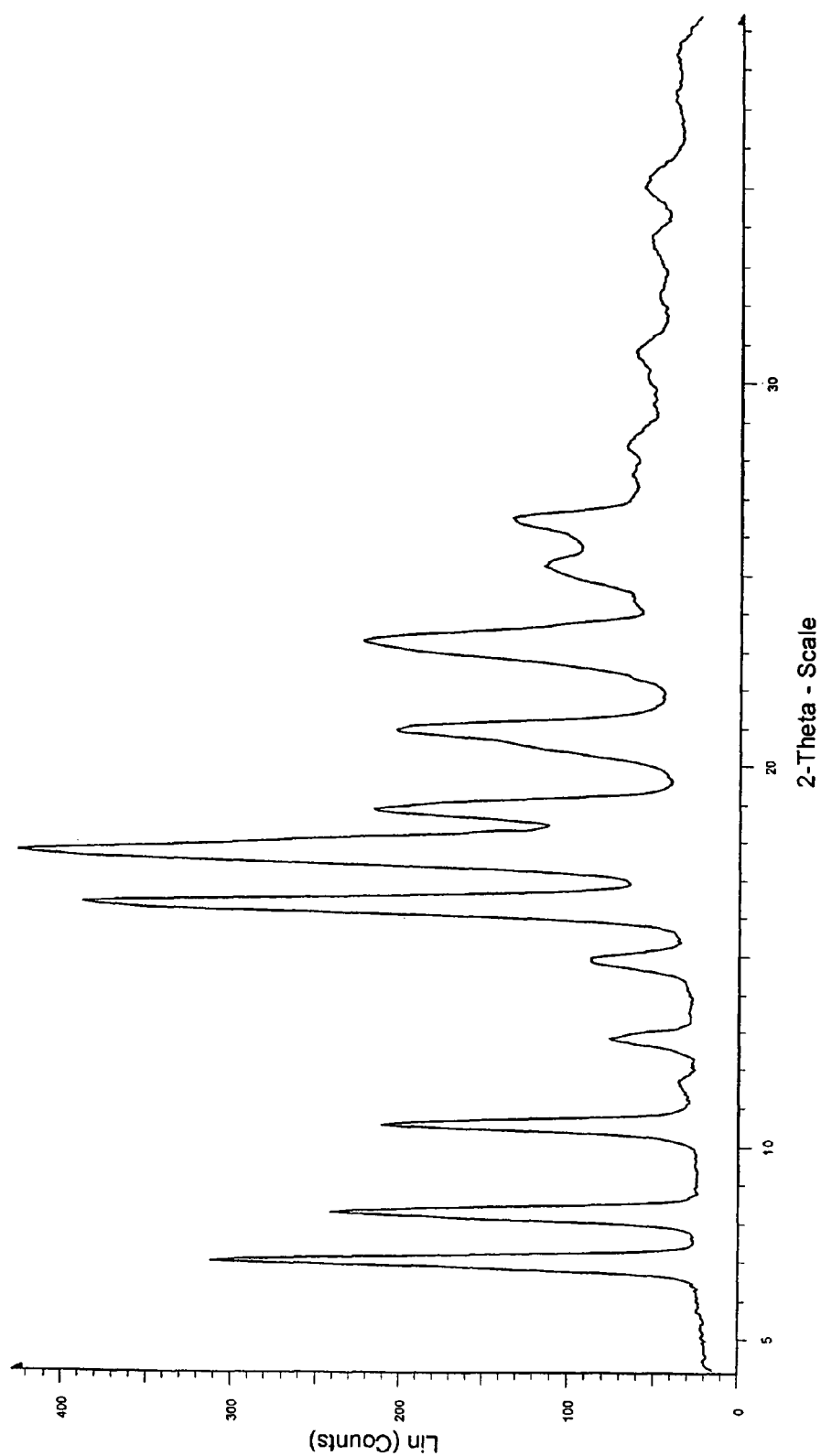

| | | | |
|---|---|---|---|
| 7,511,158 | B2 | 3/2009 | Gallop et al. |
| 7,662,987 | B2 | 2/2010 | Bhat et al. |
| 7,700,652 | B2 | 4/2010 | Barrett et al. |
| 2003/0176398 | A1 | 9/2003 | Gallop et al. |
| 2004/0254246 | A1 | 12/2004 | Barrett et al. |
| 2005/0090550 | A1 | 4/2005 | Barrett |
| 2005/0192353 | A1 | 9/2005 | Barrett |
| 2005/0209319 | A1 | 9/2005 | Cundy et al. |
| 2006/0141034 | A1 | 6/2006 | Cundy et al. |
| 2008/0161393 | A1 | 7/2008 | Barrett et al. |
| 2008/0188562 | A1 | 8/2008 | Zerangue |
| 2009/0216037 | A1 | 8/2009 | Gallop et al. |
| 2010/0056632 | A1 | 3/2010 | Estrada et al. |
| 2010/0166825 | A1 | 7/2010 | Barrett |
| 2010/0267946 | A1 | 10/2010 | Gallop et al. |
| 2011/0021628 | A1 | 1/2011 | Estrada et al. |

FOREIGN PATENT DOCUMENTS

| | | | |
|---|---|---|---|
| EP | 1178034 | A1 | 2/2002 |
| EP | 1201240 | A2 | 5/2002 |
| EP | 1201240 | A3 | 5/2002 |
| GB | 2362646 | A | 11/2001 |
| JP | 62258337 | A | 11/1987 |
| JP | 2002346303 | A | 12/2002 |
| JP | 2002355501 | A | 12/2002 |
| WO | WO 92/09560 | A1 | 6/1992 |
| WO | WO 93/23383 | A1 | 11/1993 |
| WO | WO 97/29101 | A1 | 8/1997 |
| WO | WO 97/33858 | | 9/1997 |
| WO | WO 97/33858 | A1 | 9/1997 |
| WO | WO 97/33859 | A1 | 9/1997 |
| WO | WO 98/17627 | A1 | 4/1998 |
| WO | WO 99/08671 | A1 | 2/1999 |
| WO | WO 99/21824 | A1 | 5/1999 |
| WO | WO 99/31057 | A1 | 6/1999 |
| WO | WO 99/31074 | A2 | 6/1999 |
| WO | WO 99/31074 | A3 | 6/1999 |
| WO | WO 99/31075 | A1 | 6/1999 |
| WO | WO 99/37296 | A1 | 7/1999 |
| WO | WO 99/61424 | A1 | 12/1999 |
| WO | WO 99/64213 | A1 | 12/1999 |
| WO | WO 00/23067 | A1 | 4/2000 |
| WO | WO 00/31020 | A1 | 6/2000 |
| WO | WO 00/50027 | A1 | 8/2000 |
| WO | WO 00/61135 | | 10/2000 |
| WO | WO 01/90052 | | 11/2001 |
| WO | WO 02/00209 | A2 | 1/2002 |
| WO | WO 02/00209 | A3 | 1/2002 |
| WO | WO 02/100347 | A2 | 1/2002 |
| WO | WO 02/100347 | A3 | 1/2002 |
| WO | WO 02/28411 | A1 | 4/2002 |
| WO | WO 02/28881 | A1 | 4/2002 |
| WO | WO 02/28883 | A1 | 4/2002 |
| WO | WO 02/32376 | A2 | 4/2002 |
| WO | WO 02/32376 | A3 | 4/2002 |
| WO | WO 02/42414 | A2 | 5/2002 |
| WO | WO 02/42414 | A3 | 5/2002 |
| WO | WO 02/100347 | A2 | 12/2002 |
| WO | WO 02/100347 | A3 | 12/2002 |
| WO | WO 03/104184 | A1 | 12/2003 |
| WO | WO 2005/027850 | | 3/2005 |

OTHER PUBLICATIONS

Alderman, "A Review of Cellulose Ethers in Hydrophilic Matrices or Oral Controlled-Release Dosage Forms," *Int. J. Pharm. Tech. & Prod. Mfr.* 1984, 5(3) 1-9.

Bamba et al., "Release Mechanisms in Gelforming Sustained Release Preparations," *Int. J. Pharm.* 1979, 2, 307.

During et al., "Controlled Release of Dopamine From a Polymeric Brain Implant: In Vivo Characterization," 1989, *Ann. Neurol.* 25:351.

Goodson, "Medical Applications of Controlled Release," vol. 2, pp. 115-138 (1984).

Howard et al., "Intercerebral Drug Delivery in Rats with Lesion-Induced Memory Deficits," 1989, *J. Neurosurg.* 71:105-112.

Langer et al., "Chemical and Physical Structure of Polymers as Carriers for Controlled Release of Bioactive Agents: A Review," *J Macromol. Sci. Rev. Macromol Chem.* 1983, 23:61.

Langer, "New Method of Drug Delivery," 1990, *Science* 249:1527-1533.

Levy et al., "Inhibition of Calcification of Bioprosthetic Heart Valves by Local Controlled-Release Diphosphonate," *Science* 1985 228: 190-192.

Sefton, "Implantable Pumps," *CRC Crit Ref Biomed. Eng.* 1987, 14:201.

Verma et al., "Osmotically Controlled Oral Drug Delivery," *Drug Dev. Ind. Pharm.*, 2000, 26:695-708.

Saudek et al., "A Preliminary Trial of the Programmable Implantable Medication System for Insulin Delivery," *New England Journal of Medicine and Surgery*, 1989, 31, 574-578.

Canafax et al., Gabapentin exposure and pain reduction in patients with postherpetic neuralgia: analysis of a phase IIA randomized, double-blind, placebo-controlled study of neurontin and XP13512. Poster. (15 pages).

Ellenbogen et al., XP13512/ASP8825 improves RLS symptoms: Results of two phase II clinical studies. Poster. (15 pages).

Magnus, Nonepileptic uses of Gabapentin, *Epilepsia* 1999, 40(Suppl. 6): S66-S72.

Potschka et al., Gabapentin lactam, a close analogue of the anticonvulsant gabapentin, exerts convulsant activity in amygdala kindled rats. *Naunyn-Schmiedeberg's Arch. Pharmacol.* 2000, 361: 200-205.

Kushida et al., XP13512 improves symptoms and sleep disturbance in restless legs syndrome (RLS) patients: results of a 2 week, randomized, double blind, placebo controlled, crossover polysomnography trial. Sleep 2006: $20^{th}$ Anniversary meeting of the Associated professional Sleep Societies (APSS), Salt lake City, Utah, Jun. 17-22, 2006, Abstract 172E. (23 pages).

R&D Focus Drug News, Dec. 9, 2002, 1 page.

Final Office Action, U.S. Appl. No. 10/969,196, 15 pages, Jan. 13, 2009.

Non-Final Office Action, U.S. Appl. No. 10/940,884, 11 pages, Jan. 25, 2008.

Amendment and Response to Non-Final Office Action, U.S. Appl. No. 10/940,884, 13 pages, Jul. 25, 2008.

Final Office Action, U.S. Appl. No. 10/940,884, 8 pages, Nov. 14, 2008.

Non-Final Office Action, U.S. Appl. No. 10/940,884, 8 pages, Jan. 30, 2009.

Non-Final Office Action, U.S. Appl. No. 10/816,551, 11 pages, May 28, 2008.

Examiner Interview Summary, U.S. Appl. No. 10/816,551, 2 pages, Jul. 3, 2008.

Amendment and Response to Non-Final Office Action, U.S. Appl. No. 10/816,551, 13 pages, Aug. 28, 2008.

Final Office Action, U.S. Appl. No. 10/816,551, 10 pages, Nov. 18, 2008.

Examiner Interview Summary, U.S. Appl. No. 10/816,551, 2 pages, Feb. 12, 2009.

U.S. Appl. No. 60/606,637, filed Aug. 13, 2004, Gallop et al.

Alderman, "A Review of Cellulose Ethers in Hydrophilic Matrices or Oral Controlled-Release Dosage Forms," *Int. J. Pharm. Tech. & Prod. Mfr.* 1984, 5(3) 1-9.

Bamba et al., "Release Mechanisms in Gelforming Sustained Release Preparations," *Int. J. Pharm.* 1979, 2, 307.

During et al., "Controlled Release of Dopamine From a Polymeric Brain Implant: In Vivo Characterization," 1989, *Ann. Neurol.* 25:351.

Goodson, "Medical Applications of Controlled Release," vol. 2, pp. 115-138 (1984).

Howard et al., "Intercerebral Drug Delivery in Rats with Lesion-Induced Memory Deficits," 1989, *J. Neurosurg.* 71:105-112.

Langer et al., "Chemical and Physical Structure of Polymers as Carriers for Controlled Release of Bioactive Agents: A Review," *J Macromol. Sci. Rev. Macromol Chem.* 1983, 23:61.

Saudek et al., "A preliminary trial of the programmable implantable medication system for insulin delivery," *N Engl J Med*, 1989; 321:574-579.

Langer, "New Method of Drug Delivery," 1990, *Science* 249:1527-1533.

Levy et al., "Inhibition of Calcification of Bioprosthetic Heart Valves by Local Controlled-Release Diphosphonate," *Science* 1985 228: 190-192.

Sefton, "Implantable Pumps," *CRC Crit Ref Biomed. Eng.* 1987, 14:201.

Verma et al., "Osmotically Controlled Oral Drug Delivery," *Drug Dev. Ind. Pharm.*, 2000, 26:695-708.

Cundy et. al., "XP13512 [(±)-1-([(α-Isobutanoyloxyethoxy)carbonyl]aminomethyl)-1-cyclohexane Acetic Acid], A Novel Gabapentin Prodrug: I. Design, Synthesis, Enzymatic Conversion to Gabapentin, and Transport by Intestinal Solute Transporters," *J. Pharmacol. Exp. Ther.*, 2004; 311(1): 315-323.

Bonnet et al., Treatment of Alcohol Withdrawal Syndrome with Gabapentin, *Pharmacopsychiat.* 1999, 32, 107-109.

Byrn et al., Solid State Chemistry of Drugs, 1999, pp. 232-234, 236.

Carta et al., Gabapentin in the treatment of bipolar depression in patients with systemic lupus erythematosus, *Clin. Exp. Rheumatol.* 2004, 22(2), 266.

Crystalline and Amorphous Solids, http://www.utmem.edu/physpharm/.003a.html, Nov. 7, 2008 (2 pages).

Karam-Hage et al., Open pilot study of gabapentin versus trazodone to treat insomnia in alcoholic outpatients, *Psychiatry Clin. Neurosci.* 2003, 57, 542-544.

Lam, J., Stability Report Open Dish of API-Lonza Batch 44 Crystalline vs. Non-crystalline XP13512, XenoPort, Inc. Internal Document, 2008 (9 pages).

Menigaux et al., Preoperative Gabapentin Decreases Anxiety and Improves Early Functional Recovery from Knee Surgery, *Anesth. Analg.* 2005, 100, 1394-1399.

Prescrire Editorial Staff, Pregabalin, Very Similar to Gabapentin, *Prescrire International* 2005, 14(80), 203-206.

Turan et al., Gabapentin: An Alternative to the Cyclooxygenase-2 Inhibitors for Perioperative Pain Management, *Anesth. Analg.* 2006, 102, 175-181.

Vippagunta et al., Crystalline Solids, *Adv. Drug Del. Rev.* 2001, 48, 3-26.

West, Solid State Chemistry and its Applications, Wiley, New York (1988), pp. 358 & 365.

Non-Final Office Action, U.S. Appl. No. 11/269,045, 9 pages, Dec. 10, 2008.

Khimicheskii entsiklopedicheskii slovar (Chemical Encyclopedic Dictionary), Knunyantz, I.L. et al., eds., "Sovetskaya Entsiklopedia" (1983), pp. 130-131. (translation is 6 pages).

Ugryumov, PG "Organischeskii sintez v promyshlennosti" (Industrial Organic Synthesis), Krymizdat Typolytography, Simferopol, Kirova (1955), pp. 20-29. (translation is 12 pages).

Restriction Requirement, U.S. Appl. No. 10/816,551, 9 pages, Jul. 9, 2007.

Amendment and Response to Non-Final Office Action, U.S. Appl. No. 10/816,551, 16 pages, Aug. 28, 2008.

Notice of Allowance, U.S. Appl. No. 10/816,551, 8 pages, Aug. 7, 2009.

Non-final Office Action, U.S. Appl. No. 10/816,551, 8 pages, May 25, 2010.

Final Office Action, U.S. Appl. No. 10/816,551, 8 pages, Nov. 16, 2010.

Interview Summary, U.S. Appl. No. 10/816,551, 2 pages, Feb. 12, 2009.

Preliminary Amendment, U.S. Appl. No. 12/548,200, 12 pages, Aug. 26, 2009.

Non-Final Office Action, U.S. Appl. No, 12/548,200, 17 pages, Apr. 2, 2010.

Preliminary Amendment, U.S. Appl. No, 12/897,567, 12 pages, Oct. 4, 2010.

Non-Final Office Action, U.S. Appl. No, 12/897,567, 26 pages, Dec. 20, 2010.

Amendment and Response to Non-Final Office Action, U.S. Appl. No. 10/940,884, 17 pages, Jul. 25, 2008.

Final Office Action, U.S. Appl. No, 10/940,884, 9 pages, Nov. 14, 2008.

Non-Final Office Action, U.S. Appl. No. 10/940,884, 9 pages, Jan. 30, 2009.

Amendment and Response to Non-Final Office Action, U.S. Appl. No. 10/940,884, 23 pages, Jul. 30, 2009.

Restriction Requirement, U.S. Appl. No. 10/940,884, dated Apr. 26, 2007.

Notice of Allowance, U.S. Appl. No, 10/940,884, dated Nov. 30, 2009.

Amendment and Response to Non-Final Office Action, U.S. Appl. No. 10/969,196, 28 pages, Oct. 2, 2008.

Office Action, U.S. Appl. No. 10/969,196, dated Apr. 18, 2007.

Office Action, U.S. Appl. No. 10/969,196, dated Apr. 2, 2008.

Final Office Action, U.S. Appl. No. 10/969,196, 21 pages, Jan. 13, 2009.

Office Action, U.S. Appl. No. 10/969,196, dated Oct. 5, 2009.

Office Action, U.S. Appl. No. 10/969,196, dated Sep. 29, 2010.

MDS Pharma Services, Preformulation Summary Report for XP13512 Drug Substance, Project No. 76-002-02, 21 pages.

Pharm-Eco Certificate of Analysis, 2 pages, Jul. 23, 2003.

Bonnet et al., Treatment of Alcohol Withdrawal Syndrome with Gabapentin, Pharmacopsychiatry, May 1999, 32(3): 107-9.

Canafax et al., "Gabapentin Exposure and Pain Reduction in Patients With Postherpetic Neuralgia: Analysis of a Phase 2A Randomized, Double-Blind, Placebo-Controlled Study of Neurontin® and XP13512". Poster, 6 pages.

Ellenbogen et al., XP13512/ASP8825 improves RLS symptoms: Results of two phase II clinical studies. Poster. (14 pages).

Guttuso et al., Gabapentin's Effects on Hot Flashes in Postmenopausal Women. A Randomized Controlled Trial, Obstet Gynecol. 2003, 101: 337-345.

Karam-Hage et al., Open pilot study of gabapentin versus trazodone to treat insomnia in alcoholic outpatients, Psychiatry Clin. Neurosci., Oct. 2003, 57(5): pp. 542-544.

Larner, Neurite Growth-inhibitory Properties of Amyloid Beta-peptides in vitro: A Beta 25-35, but not A Beta 1-40, is Inhibitory, Neurosci Res Commun, 20: 147 (1997).

Meda et al., Activation of microglial cells by beta-amyloid protein and interferon-gamma, Nature 374: 647 (1995).

Potschka et al., 2000, Nauyn-Schmiedeberg's Archives of Pharmacology, vol. 361, pp. 200-205.

Rowbotham et al., Gabapentin for the Treatment of Postherpetic Neuralgia; A Randomized Controlled Trial, JAMA 1998, 280: 1837-42.

Stability Report Open Dish of API-Lonza Batch 44 Crystalline vs. Non-crystallinne XP13512.

St George-Hyslop et al, Alzheimer's disease: Antibody clears senile plaques, Nature, 400: 116 (1999).

XenoPort Laboratory Notebook 340, p. 89.
XenoPort Laboratory Notebook 361, pp. 65-66 and 70-71.
XenoPort Laboratory Notebook 361, pp. 65 and 70.
XenoPort Laboratory Notebook 361, pp. 68-69.
XenoPort Laboratory Notebook 410, p. 56.
XenoPort Laboratory Notebook 431, pp. 29 and 31.
XenoPort Laboratory Notebook 466, p. 35.
XenoPort Laboratory Notebook 466, p. 50.
XenoPort Laboratory Notebook 488, p. 10.
XenoPort Laboratory Notebook 530, p. 69.
XenoPort Laboratory Notebook 530, p. 70.
XenoPort Laboratory Notebook 530, p. 72 and Notebook 466, p. 81.
XenoPort Laboratory Notebook 530, pp. 56 and 71.
XenoPort Laboratory Notebook 535, p. 46.
XenoPort Laboratory Notebook Unknown, p. 45.
XenoPort Laboratory Notebook 430 p. 45.

* cited by examiner

CRYSTALLINE FORM OF γ-AMINOBUTYRIC ACID ANALOG

This application claims the benefit under 35 U.S.C. §119 (e) of U.S. Provisional Application Ser. No. 60/511,287, filed Oct. 14, 2003.

1. FIELD

Disclosed herein is a crystalline form of an analog of γ-aminobutyric acid and methods of making the crystalline form thereof. These analogs may be used as therapeutic agents in the treatment of certain diseases and disorders, including, for example, neuropathic pain and post-herpetic neuralgia.

2. BACKGROUND

In general, crystalline forms of drugs are preferred over amorphous forms of drugs, in part, because of their superior stability. For example, in many situations, an amorphous drug converts to a crystalline drug form upon storage. Because amorphous and crystalline forms of a drug typically have differing physical/chemical properties, potencies and/or bioavailabilities, such interconversion is undesirable for safety reasons in pharmaceutical administration. A key characteristic of any crystalline drug substance is the polymorphic behavior of such a material. Polymorphs are crystals of the same molecule which have different physical properties because the crystal lattice contains a different arrangement of molecules. The different physical properties exhibited by polymorphs affect important pharmaceutical parameters such as storage, stability, compressibility, density (important in formulation and product manufacturing) and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, the physical properties of the crystalline form may be important in pharmaceutical processing. For example, a particular crystalline form may form solvates more readily or may be more difficult to filter and wash free of impurities than other forms (i.e., particle shape and size distribution might be different between one crystalline form relative to other forms).

Agencies such as the United States Food and Drug Administration closely regulate the polymorphic content of the active component of a drug in solid dosage forms. In general, the regulatory agency requires batch-by-batch monitoring for polymorphic drugs if anything other than the pure, thermodynamically preferred polymorph is marketed. Accordingly, medical and commercial reasons favor synthesizing and marketing solid drugs as the thermodynamically stable polymorph, substantially free of kinetically favored polymorphs.

1-{[(α-Isobutanoyloxyethoxy)carbonyl]aminomethyl}-1-cyclohexane acetic acid, (1), a prodrug of the GABA analog gabapentin (2), has high bioavailability as gabapentin when dosed either orally or directly into the colon of a mammal (Gallop et al., International Publication No. WO 02/100347). The high bioavailability makes compound (1) a valuable component of oral dosage forms (including sustained-release dosage forms) useful for treating or preventing epilepsy, pain (especially, neuropathic pain and muscular and skeletal pain), depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome.

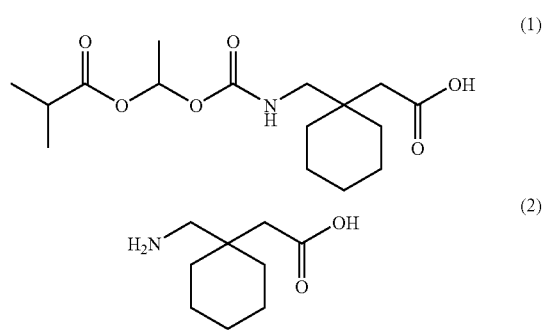

Compound (1), prepared as described in Gallop et al., International Publication No. WO 02/100347, is isolated as a glassy solid after lyophilization from aqueous acetonitrile. The material obtained by this process is partially or wholly amorphous and certain alkali metal salt forms are hygroscopic. However, amorphous solids and particularly hygroscopic solids are difficult to handle under pharmaceutical processing conditions because of low bulk densities and unsatisfactory flow properties. Moreover, handling of hygroscopic solids requires special techniques and equipment to obtain, for example, reproducible amounts of active compound or solid formulation stability. Furthermore, drugs that are hygroscopic must be packaged in special containers that have water vapor barriers thus substantially increasing the cost of such products.

Accordingly, a need exists for crystalline forms of 1-{[(α-isobutanoyloxyethoxy)carbonyl]aminomethyl}-1-cyclohexane acetic acid with superior physicochemical properties that may be used advantageously in pharmaceutical processing and pharmaceutical compositions.

3. SUMMARY

A crystalline form of 1-{[(α-isobutanoyloxyethoxy)carbonyl]aminomethyl}-1-cyclohexane acetic acid is provided that satisfies these and other needs. Also provided are pharmaceutical compositions of a crystalline form of 1-{[(α-isobutanoyloxyethoxy)carbonyl]aminomethyl}-1-cyclohexane acetic acid, methods of using the crystalline form of 1-{[(α-isobutanoyloxyethoxy)carbonyl]aminomethyl}-1-cyclohexane acetic acid and pharmaceutical compositions thereof to treat or prevent various diseases and methods of making crystalline forms of 1-{[(α-isobutanoyloxyethoxy)carbonyl]aminomethyl}-1-cyclohexane acetic acid.

In a first aspect, crystalline 1-{[(α-isobutanoyloxyethoxy)carbonyl]-aminomethyl}-1-cyclohexane acetic acid is provided that has characteristic absorption peaks (2θ) at 7.0°±0.3°, 8.2°±0.3°, 10.5°±0.3+, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3° in an X-ray powder diffractogram.

In a second aspect, pharmaceutical compositions of the crystalline form of 1-{[(α-isobutanoyloxyethoxy)carbonyl]

aminomethyl}-1-cyclohexane acetic acid are provided. The pharmaceutical compositions comprise 1-{[(α-isobutanoyloxyethoxy)carbonyl]aminomethyl}-1-cyclohexane acetic acid that has characteristic absorption peaks (2θ) at 7.0°±0.3°, 8.2°±0.3°, 10.5°±0.3°, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3° in an X-ray powder diffractogram and a pharmaceutically acceptable vehicle.

In a third aspect, methods for treating or preventing epilepsy, pain (especially, neuropathic pain and muscular and skeletal pain), depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome are provided. The methods generally involve administering to a patient in need of such treatment or prevention a therapeutically effective amount of 1-{[(α-isobutanoyloxyethoxy)carbonyl]-aminomethyl}-1-cyclohexane acetic acid that has characteristic absorption peaks (2θ) at 7.0°±0.3°, 8.2°±0.3°, 10.5°±0.3°, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3° in an X-ray powder diffractogram.

In a fourth aspect, pharmaceutical compositions for treating or preventing epilepsy, pain (especially, neuropathic pain and muscular and skeletal pain), depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome in a patient in need of such treatment or prevention are provided. The methods generally involve administering to a patient in need of such treatment or prevention a therapeutically effective amount of a pharmaceutical composition of 1-{[(α-isobutanoyloxyethoxy)carbonyl]-aminomethyl}-1-cyclohexane acetic acid that has characteristic absorption peaks (2θ) at 7.0°±0.3°, 8.2°±0.3°, 10.5°±0.3°, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3° in an X-ray powder diffractogram.

In a fifth aspect, methods for making crystalline 1-{[(α-isobutanoyloxyethoxy)carbonyl]aminomethyl}-1-cyclohexane acetic acid that has characteristic absorption peaks (2θ) at 7.0°±0.3°, 8.2°±0.3°, 10.5°±0.3°, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3° in an X-ray powder diffractogram are provided.

4. BRIEF DESCRIPTION OF THE FIGURES

Figure 2:
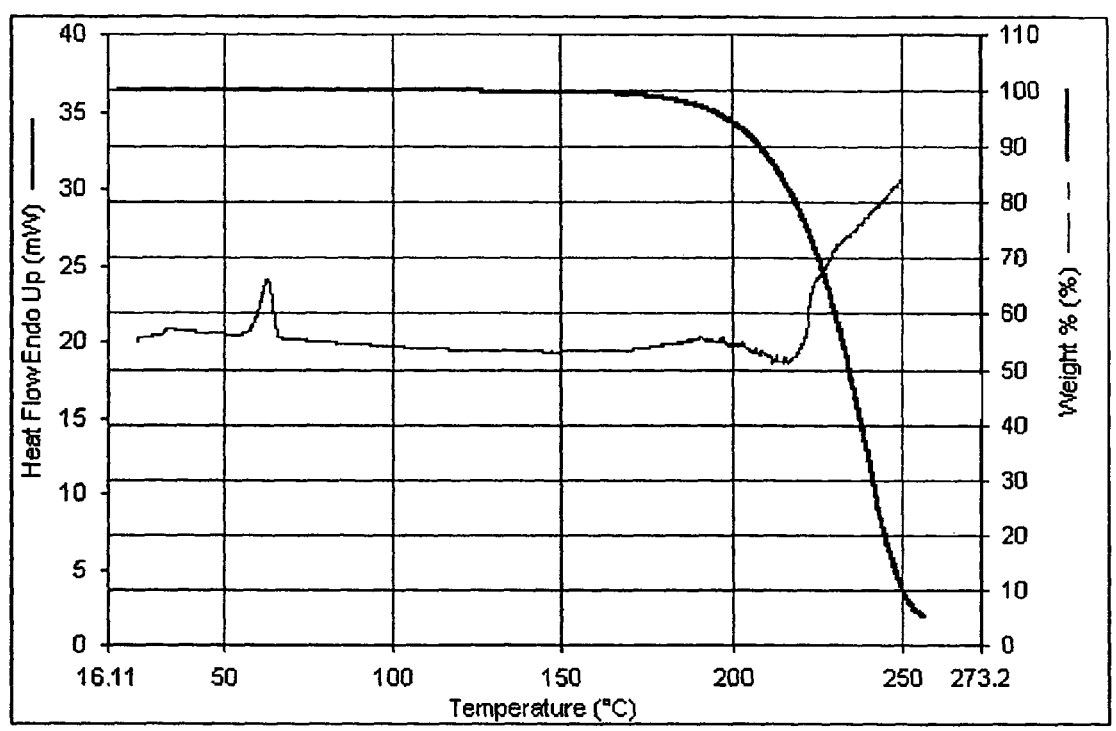

FIG. 1 illustrates an X-ray powder diffractogram of crystalline 1-{[(α-isobutanoyloxyethoxy)carbonyl]aminomethyl}-1-cyclohexane acetic acid; and FIG. 2 illustrates a differential scanning calorimetery thermogram of crystalline 1-{[(α-isobutanoyloxyethoxy)carbonyl]aminomethyl}-1-cyclohexane acetic acid.

5. DETAILED DESCRIPTION

5.1 Definitions

"Pharmaceutically acceptable vehicle" refers to a diluent, adjuvant, excipient or carrier with which 1-{[(α-isobutanoyloxyethoxy)carbonyl]aminomethyl}-1-cyclohexane acetic acid is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments. Although preferred embodiments are described, it will be understood that the invention is not limited to those preferred embodiments. To the contrary, it is intended to cover alternatives, modifications and equivalents as may be included within the spirit and scope of the invention as defined by any claim(s) issuing herefrom.

5.2 Crystalline Forms of 1-{[(α-Isobutanoyloxyethoxy)carbonyl]aminomethyl}-1-Cyclohexane Acetic Acid and Preparation Thereof Crystalline forms of 1-{[(α-isobutanoyloxyethoxy)carbonyl]aminomethyl}-1-cyclohexane acetic acid and methods of making crystalline forms of 1-{[(α-isobutanoyloxyethoxy)carbonyl]aminomethyl}-1-cyclohexane acetic acid are disclosed in detail herein.

It should be understood that referral to 1-{[(α-isobutanoyloxyethoxy)carbonyl]aminomethyl}-1-cyclohexane acetic acid includes all substantially racemic mixtures, all possible tautomeric forms of the conventional chemical structure for this compound and all isotopically labeled derivatives of this compound (e.g., $^2$H, $^3$H, $^{13}$C, $^{14}$C, $^{15}$N, $^{17}$O, $^{18}$O, etc.).

The starting material (i.e., 1-{[(α-isobutanoyloxyethoxy)carbonyl]aminomethyl}-1-cyclohexane acetic acid) can be made according to procedures disclosed in Example 13 of Gallop et al., International Publication No. WO 02/100347 or Example 12 of Gallop et al., U.S. Provisional Patent Application Ser. No. 60/606,637, filed Aug. 13, 2004, entitled, "Methods for Synthesis of Acyloxyalkyl Carbamate Prodrugs."

In one aspect, crystalline 1-{[(α-isobutanoyloxyethoxy)carbonyl]-aminomethyl}-1-cyclohexane acetic acid is provided. In some embodiments, crystalline 1-{[(α-isobutanoyloxyethoxy)carbonyl]-aminomethyl}-1-cyclohexane acetic acid has characteristic absorption peaks at 7.0°±0.3°, 8.2°±0.3°, 10.5°±0.3°, 12.8°±0.3°, 14.9°±0.3°, 16.4°±0.3°, 17.9°±0.3°, 18.1°±0.3°, 18.9°±0.3°, 20.9°±0.3°, 23.3°±0.3°, 25.3°±0.3° and 26.6°±0.3°. In other embodiments, crystalline 1-{[(α-isobutanoyloxyethoxy)carbonyl]-aminomethyl}-1-cyclohexane acetic acid has characteristic absorption peaks at 7.0°±0.2°, 8.2°±0.2°, 10.5°±0.2°, 12.8°±0.2°, 14.9°±0.2°, 16.4°±0.2°, 17.9°±0.2°, 18.1°±0.2°, 18.9°±0.2°, 20.9°±0.2°, 23.3°±0.2°, 25.3°±0.2°, and 26.6°±0.2° in an X-ray powder diffractogram.

In some embodiments, crystalline 1-{[(α-isobutanoyloxyethoxy)carbonyl]aminomethyl}-1-cyclohexane acetic acid melts between about 54° C. and about 78° C. In other embodiments, crystalline 1-{[(α-isobutanoyloxyethoxy)carbonyl]aminomethyl}-1-cyclohexane acetic acid melts between about 58° C. and about 70° C. In still other embodiments, crystalline 1-{[(α-isobutanoyloxyethoxy)carbonyl]aminomethyl}-1-cyclohexane acetic acid melts between about 62° C. and about 68° C. In still other embodiments, crystalline 1-{[(α-isobutanoyloxyethoxy)carbonyl]aminomethyl}-1-cyclohexane acetic acid melts between about 62° C. and about 66° C. In still other embodiments, crystalline 1-{[(α-isobutanoyloxyethoxy)carbonyl]aminomethyl}-1-cyclohexane acetic acid melts between about 63° C. and about 66° C. In still other embodiments, crystalline 1-{[(α-isobutanoyloxyethoxy)carbonyl]aminomethyl}-1-cyclohexane acetic acid melts between about 64° C. and about 66° C. In still other embodiments, crystalline 1-{[(α-isobutanoyloxyethoxy)carbonyl]aminomethyl}-1-cyclohexane acetic acid melts between about 63° C. and about 64° C. In some embodiments, crystalline 1-{[(α-isobutanoyloxyethoxy)carbonyl]-aminomethyl}-1-cyclohexane acetic acid may be prepared by first adding 1-{[(α-isobutanoyloxyethoxy)carbonyl]aminomethyl}-1-cyclohexane acetic acid to a solvent to form a solution or suspension. As used herein, the terms solution and suspension are used interchangeably and are meant to include circumstances where 1-{[(α-isobutanoyloxyethoxy)carbonyl]aminomethyl}-1-cyclohexane acetic acid is placed in a solvent or solvent mixture regardless of solubility. The solvent used in crystallization may be either a homogenous solvent, a combination of solvents, or a solvent or solvent combination in which the 1-{[(α-isobutanoyloxyethoxy)carbonyl]aminomethyl}-1-cyclohexane acetic acid exhibits temperature dependent solubility. In general, solvents or solvent combinations in which 1-{[(α-isobutanoyloxyethoxy)carbonyl]aminomethyl}-1-cyclohexane acetic acid is soluble within a first temperature range, and poorly soluble within a second temperature range, can be advantageously used in the methods described herein. Mixtures of a "good" solvent and an "anti-solvent" can also be used with temperature dependent solubilization, i.e., dissolving at elevated temperature and crystallizing at room temperature. Examples of suitable "good" solvents include methanol, ethanol, 1,2-propane diol, t-butanol, n-butanol, isopropanol, acetic acid, nitromethane, acetonitrile, dimethylsulfoxide, dimethylformamide, N-methyl pyrrolidone, acetone, methyl acetate, ethyl acetate, isopropyl acetate, isobutyl acetate, methyl isobutyl ketone, 1,2-dimethoxyethane, tetrahydrofuran, 2-methyl tetrahydrofuran, toluene, methyl t-butyl ether, chlorobenzene, 1,4-dioxane, diethylether, cumene, o-xylene, m-xylene, p-xylene, 2-ethoxyethanol, 1,2-ethandiol, ethyl formate, 2-methoxyethanol, 1-pentanol, anisole, dichloromethane, cis and trans 1,2 dichloroethylene, chloroform, dimethylacetamide, propylacetate and mixtures thereof. Examples of suitable "anti-solvents" include alkanes such as pentane, hexane, heptane, octane, nonane, decane, undecane, dodecane, cis- or trans-decalin, cyclohexane, methylcyclohexane and mixtures thereof.

Preferably, the dissolution process is carried out at elevated temperature, up to and including the boiling point of the solvent or solvent combination. Accordingly, in some embodiments, 1-{[(α-isobutanoyloxyethoxy)carbonyl]aminomethyl}-1-cyclohexane acetic acid is dissolved in a solvent or solvent mixture with heating and optionally, with shaking and stirring. The heated solution may be kept at elevated temperature to ensure complete dissolution of 1-{[(α-isobutanoyloxyethoxy)carbonyl]aminomethyl}-1-cyclohexane acetic acid. The heated solution may also be filtered at elevated temperature to remove any undissolved components.

Preferably, the solution is cooled slowly to provide crystalline 1-{[(α-isobutanoyloxyethoxy)carbonyl]aminomethyl}-1-cyclohexane acetic acid, which may be separated from residual solvent by filtration and/or drying under reduced pressure. In some embodiments, the solution is cooled between about 0° C. and about 25° C. Other methods, known to those of skill in the crystallization arts, (e.g., solvent evaporation, drowning, chemical reaction, seeding with a small quantity of the desired crystal form, etc.) may also be employed to provide crystalline 1-{[(α-isobutanoyloxyethoxy)carbonyl]aminomethyl}-1-cyclohexane acetic acid.

In some embodiments, 1-{[(α-isobutanoyloxyethoxy)carbonyl]aminomethyl}-1-cyclohexane acetic acid is dissolved in heptane at a temperature between about 70° C. and about reflux temperature. Preferably, the temperature is about 70° C. and the concentration of 1-{[(α-isobutanoyloxyethoxy)carbonyl]aminomethyl}-1-cyclohexane acetic acid in heptane is between about 0.07 g/mL to about 0.08 g/mL. The solution is then cooled to room temperature to provide crystalline 1-{[(α-isobutanoyloxyethoxy)carbonyl]aminomethyl}-1-cyclohexane acetic acid.

In other embodiments, 1-{[(α-isobutanoyloxyethoxy)carbonyl]-aminomethyl}-1-cyclohexane acetic acid is dissolved in a mixture of heptane/ethyl acetate (10:1 by volume) at a temperature between about 50° C. and about the reflux temperature, more preferably at a temperature of about 70° C. The concentration of 1-{[(α-isobutanoyloxyethoxy)carbonyl]-aminomethyl}-1-cyclohexane acetic acid in the heptane/ethyl acetate mixture is between about 0.18 g/mL to about 0.22 g/mL. The solution is then cooled to between about 0° C. and about 25° C. to provide crystalline 1-{[(α-isobutanoyloxyethoxy)carbonyl]aminomethyl}-1-cyclohexane acetic acid.

In yet other embodiments, 1-{[(α-isobutanoyloxyethoxy)carbonyl]-aminomethyl}-1-cyclohexane acetic acid is dissolved in a mixture of methylcyclohexane/methyl t-butyl ether (the volumetric ratio of methylcyclohexane- to methyl t-butyl ether between about 5:1 to about 20:1, preferably, around 10:1) at a temperature between about 20 and about 40° C. and the concentration of 1-{[(α-isobutanoyloxyethoxy)carbonyl]-aminomethyl}-1-cyclohexane acetic acid in the methylcyclohexane/methyl t-butyl ether mixture is between about 0.1 g/mL to about 0.25 g/mL. The solution is then cooled to between about 0° C. and about 25° C. to provide crystalline 1-{[(α-isobutanoyloxyethoxy)carbonyl]aminomethyl}-1-cyclohexane acetic acid.

5.3 Therapeutic Uses

Crystalline forms of 1-{[(α-isobutanoyloxyethoxy)carbonyl]aminomethyl}-1-cyclohexane acetic acid and/or pharmaceutical compositions thereof may be administered to a patient, preferably a human, suffering from epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome. Further, in certain embodiments, crystalline forms of 1-{[(α-isobutanoyloxyethoxy)carbonyl]aminomethyl}-1-cyclohexane acetic acid and/or pharmaceutical compositions thereof are administered to a patient, preferably a human, as a preventative measure against various diseases or disorders. Crystalline forms of 1-{[(α-isobutanoyloxyethoxy)carbonyl]aminomethyl}-1-cyclohexane acetic acid and/or pharmaceutical compositions thereof may be administered as a preventative measure to a patient having a predisposition for epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome. Accordingly, crystalline forms of 1-{[(α-isobutanoyloxyethoxy)carbonyl]aminomethyl}-1-cyclohexane acetic acid and/or pharmaceutical compositions thereof may be used for the prevention of one disease or disorder and concurrently treating another (e.g., prevention of psychosis while treating gastrointestinal disorders; prevention of neuropathic pain while treating ethanol withdrawal syndrome).

The suitability of crystalline forms of 1-{[(α-isobutanoyloxyethoxy)carbonyl]-aminomethyl}-1-cyclohexane acetic acid and/or pharmaceutical compositions thereof in treating epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome may be determined by methods known in the art (e.g., Satzinger et al., U.S. Pat. No. 4,024,175; Satzinger et al., U.S. Pat. No. 4,087,544; Woodruff, U.S. Pat. No. 5,084,169; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bellioti, International Publication No. WO 00/31020; Bryans et al., International Publication No. WO 00/50027; and Bryans et al., International Publication No. WO 02/00209). Crystalline forms of 1-{[(α-isobutanoyloxyethoxy)carbonyl]aminomethyl}-1-cyclohexane acetic acid and/or pharmaceutical compositions thereof may be used to treat or prevent epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome using known procedures described in the art (see references above).

The compound disclosed herein, may be more efficacious than the parent drug molecule (e.g., gabapentin or other GABA analog) in treating or preventing epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome because the disclosed compound may require less time to reach a therapeutic concentration in the blood, i.e., the compound disclosed herein has a shorter $t_{max}$ than gabapentin when taken orally. Without wishing to bound by theory, it is believed that the compound disclosed herein is absorbed from the gastrointestinal lumen into the blood by a different mechanism than that by which gabapentin and other known GABA analogs are absorbed. For example, gabapentin is believed to be actively transporter across the gut wall by a carrier transporter localized in the human small intestine. The gabapentin transporter is easily saturated which means that the amount of gabapentin absorbed into the blood is not proportional to the amount of gabapentin that is administer orally, since once the transport mechanism is saturated, further absorption of gabapentin does not occur to any significant degree. In comparison to gabapentin, the compound disclosed herein, is absorbed across the gut wall along a greater portion of the gastrointestinal tract, including the colon.

Because the compound disclosed herein can be formulated in sustained release formulations which provides for sustained release over a period of hours into the gastrointestinal tract and particularly, release within the colon, 1-{[(α-isobutanoyloxyethoxy)carbonyl]aminomethyl}-1-cyclohexane acetic acid may also be more efficacious than gabapentin in treating or preventing epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome. The ability of the compound disclosed herein to be used in sustained release oral dosage forms reduces the dosing frequency necessary for maintenance of a therapeutically effective drug concentration in the blood.

5.4 Modes of Administration

Crystalline forms of 1-{[(α-isobutanoyloxyethoxy)carbonyl]aminomethyl}-1-cyclohexane acetic acid and/or pharmaceutical compositions thereof may be advantageously used in human medicine. As previously described, crystalline forms of 1-{[(α-isobutanoyloxyethoxy)carbonyl]aminomethyl}-1-cyclohexane acetic acid and/or pharmaceutical compositions thereof are useful for the treatment or prevention of epilepsy, pain (especially, neuropathic pain and muscular and skeletal pain), post-herpetic neuralgia, depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome.

When used to treat or prevent the above disease or disorders, crystalline forms of 1-{[(α-isobutanoyloxyethoxy)carbonyl]aminomethyl}-1-cyclohexane acetic acid and/or pharmaceutical compositions thereof may be administered or applied singly, or in combination with other agents. Crystalline forms of 1-{[(α-isobutanoyloxyethoxy)carbonyl]aminomethyl}-1-cyclohexane acetic acid and/or pharmaceutical compositions thereof may also be administered or applied singly or in combination with other pharmaceutically active agents, including other GABA analogs.

Methods of treatment and prophylaxis are provided by administration to a patient of a therapeutically effective amount of a crystalline form of 1-{[(α-isobutanoyloxyethoxy)carbonyl]aminomethyl}-1-cyclohexane acetic acid and/or pharmaceutical compositions thereof. The patient may be an animal, is more preferably, a mammal, and most preferably, a human.

Crystalline forms of 1-{[(α-isobutanoyloxyethoxy)carbonyl]aminomethyl}-1-cyclohexane acetic acid and/or pharmaceutical compositions thereof, are preferably administered orally. Crystalline forms of 1-{[(α-isobutanoyloxyethoxy)carbonyl]-aminomethyl}-1-cyclohexane acetic acid and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer crystalline forms of 1-{[(α-isobutanoyloxyethoxy)carbonyl]aminomethyl}-1-cyclohexane acetic acid and/or pharmaceutical compositions thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin.

In some embodiments, crystalline forms of 1-{[(α-isobutanoyloxyethoxy)carbonyl]aminomethyl}-1-cyclohexane acetic acid and/or pharmaceutical compositions thereof can be delivered via sustained release systems, preferably, oral sustained release systems. In one embodiment, a pump may be used (Langer, supra; Sefton, 1987, *CRC Crit Ref. Biomed. Eng.* 14:201; Saudek et al., 1989, *N. Engl. J. Med.* 321:574).

In other embodiments, polymeric materials can be used ("Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J. Macromol. Sci. Rev. Macromol. Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for oral sustained release delivery. Polymers include, for example, sodium carboxymethylcellulose, hydroxypropylcellulose, hydroxypropylmethylcellulose and hydroxyethylcellulose (preferably, hydroxypropylmethylcellulose). Other cellulose ethers have been described (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2, 307).

In other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.* 2000, 26:695-708). In some embodiments, OROS™ osmotic devices are used for oral sustained release delivery devices (Theeuwes et al., U.S. Pat. No. 3,845,770; Theeuwes et al., U.S. Pat. No. 3,916,899).

In yet other embodiments, a controlled-release system can be placed in proximity of the target of crystalline forms of 1-{[(α-isobutanoyloxyethoxy)carbonyl]aminomethyl}-1-cyclohexane acetic acid and/or pharmaceutical compositions thereof, thus requiring only a fraction of the systemic dose (e.g., Goodson, in "Medical Applications of Controlled Release," supra, vol. 2, pp. 115-138 (1984)). Other controlled-release systems discussed in Langer, 1990, *Science* 249:1527-1533 may also be used.

Crystalline forms of 1-{[(α-isobutanoyloxyethoxy)carbonyl]aminomethyl}-1-cyclohexane acetic acid and/or pharmaceutical compositions thereof preferably, provide gabapentin upon in vivo administration to a patient. While not wishing to bound by theory, the promoiety of crystalline forms of 1-{[(α-isobutanoyloxyethoxy)carbonyl]aminomethyl}-1-cyclohexane acetic acid and/or pharmaceutical compositions thereof may be cleaved either chemically and/or enzymatically. One or more enzymes present in the stomach, intestinal lumen, intestinal tissue, blood, liver, brain or any other suitable tissue of a mammal may cleave the promoiety of crystalline forms of 1-{[(α-isobutanoyloxyethoxy)carbonyl]aminomethyl}-1-cyclohexane acetic acid and/or pharmaceutical compositions thereof. The mechanism of cleavage is not important. Preferably, gabapentin formed by cleavage of promoieties from the crystalline form of 1-{[(α-isobutanoyloxyethoxy)carbonyl]aminomethyl}-1-cyclohexane acetic acid and/or pharmaceutical compositions thereof does not contain substantial quantities of γ-lactam contaminant (preferably, less than 0.5% by weight, more preferably, less than 0.2% by weight, most preferably less than 0.1% by weight) which is formed by intramolecular cyclization of the γ amino group with the carboxyl functionality. The extent of lactam formation from crystalline forms of 1-{[(α-isobutanoyloxyethoxy)carbonyl]aminomethyl}-1-cyclohexane acetic acid and/or pharmaceutical compositions thereof may be assessed using standard in vitro analytical methods.

While not wishing to bound by theory, the promoiety of crystalline forms of 1-{[(α-isobutanoyloxyethoxy)carbonyl]aminomethyl}-1-cyclohexane acetic acid and/or pharmaceutical compositions thereof may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety of crystalline forms of 1-{[(α-isobutanoyloxyethoxy)carbonyl]aminomethyl}-1-cyclohexane acetic acid and/or pharmaceutical compositions thereof is cleaved prior to absorption by the gastrointestinal tract, gabapentin may be absorbed into the systemic circulation conventionally (e.g., via the large neutral amino acid transporter located in the small intestine). If the promoiety of crystalline forms of 1-{[(α-isobutanoyloxyethoxy)carbonyl]aminomethyl}-1-cyclohexane acetic acid and/or pharmaceutical compositions thereof are cleaved after absorption by the gastrointestinal tract, this GABA analog prodrug may be absorbed into the systemic circulation either by passive diffusion, active transport or by both passive and active processes.

If the promoiety of crystalline forms of 1-{[(α-isobutanoyloxyethoxy)carbonyl]aminomethyl}-1-cyclohexane acetic acid and/or pharmaceutical compositions thereof is cleaved after absorption by the gastrointestinal tract, this GABA analog prodrug may have the opportunity to be absorbed into the systemic circulation from the large intestine. In this situation, crystalline forms of 1-{[(α-isobutanoyloxyethoxy)carbonyl]aminomethyl}-1-cyclohexane acetic acid and/or pharmaceutical compositions thereof are preferably administered as sustained release systems. In some embodiments, crystalline forms of 1-{[(α-isobutanoyloxyethoxy)carbonyl]aminomethyl}-1-cyclohexane acetic acid and/or pharmaceutical compositions thereof are delivered by oral sustained release administration. Preferably, in these embodiments, crystalline forms of 1-{[(α-isobutanoyloxyethoxy)carbonyl]aminomethyl}-1-cyclohexane acetic acid and/or pharmaceutical compositions thereof are administered twice per day (more preferably, once per day).

5.5 Pharmaceutical Compositions

The present pharmaceutical compositions contain a therapeutically effective amount of a crystalline form of 1-{[(α-isobutanoyloxyethoxy)carbonyl]aminomethyl}-1-cyclohexane acetic acid together with a suitable amount of a pharmaceutically acceptable vehicle, so as to provide the form for proper administration to a patient. When administered to a patient, crystalline forms of 1-{[(α-isobutanoyloxyethoxy)carbonyl]aminomethyl}-1-cyclohexane acetic acid and pharmaceutically acceptable vehicles are preferably sterile. Water is a preferred vehicle when a crystalline form of 1-{[(α-isobutanoyloxyethoxy)carbonyl]aminomethyl}-1-cyclohexane acetic acid is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. The present compositions, if desired, can also contain minor amounts of wetting or emulsifying agents or pH buffering agents. In addition, auxiliary, stabilizing, thickening, lubricating and coloring agents may be used.

In some embodiments, the pharmaceutical compositions of crystalline forms of 1-{[(α-isobutanoyloxyethoxy)carbonyl]aminomethyl}-1-cyclohexane acetic acid are free of lactam side products formed by intramolecular cyclization. In other embodiments, the pharmaceutical compositions of crystalline forms of 1-{[(α-isobutanoyloxyethoxy)carbonyl]aminomethyl}-1-cyclohexane acetic acid are stable to extended storage (preferably, greater than one year) without substantial lactam formation (preferably, less than 0.5% lactam by weight, more preferably, less than 0.2% lactam by weight, most preferably, less than 0.1% lactam by weight).

Pharmaceutical compositions comprising crystalline forms of 1-{[(α-isobutanoyloxyethoxy)carbonyl]aminomethyl}-1-cyclohexane acetic acid may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of crystalline forms of 1-{[(α-isobutanoyloxyethoxy)carbonyl]aminomethyl}-1-cyclohexane acetic acid into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). Compositions of crystalline forms of 1-{[(α-isobutanoyloxyethoxy)carbonyl]aminomethyl}-1-cyclohexane acetic acid are preferably formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administering the compounds and compositions disclosed herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Pharmaceutical compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a crystalline form of 1-{[(α-isobutanoyloxyethoxy)carbonyl]-aminomethyl}-1-cyclohexane acetic acid with a pharmaceutically acceptable vehicle. Preferably, the pharmaceutically acceptable vehicle is a liquid such as alcohol, water, polyethylene glycol or perfluorocarbon. Optionally, another material may be added to alter the aerosol properties of the solution or suspension of the compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A crystalline form of 1-{[(α-isobutanoyloxyethoxy)carbonyl]aminomethyl}-1-cyclohexane acetic acid may also be formulated in rectal or vaginal compositions such as suppositories or retention enemas, e.g., containing conventional suppository bases such as cocoa butter or other glycerides. In addition to the formulations described previously, a crystalline form of 1-{[(α-isobutanoyloxyethoxy)carbonyl]aminomethyl}-1-cyclohexane acetic acid may also be formulated as a depot preparation. Such long acting formulations may be administered by implantation (for example subcutaneously or intramuscularly) or by intramuscular injection. Thus, for example, a crystalline form of 1-{[(α-isobutanoyloxyethoxy)carbonyl] aminomethyl}-1-cyclohexane acetic acid may be formulated with suitable polymeric or hydrophobic materials (for example, as an emulsion in an acceptable oil) or ion exchange resins, or as sparingly soluble derivatives, for example, as a sparingly soluble salt.

In some embodiments, a crystalline form of 1-{[(α-isobutanoyloxyethoxy)carbonyl]aminomethyl}-1-cyclohexane acetic acid is formulated as a pure active agent. In other embodiments, a crystalline form of 1-{[(α-isobutanoyloxyethoxy)carbonyl]aminomethyl}-1-cyclohexane acetic acid is formulated as a mixture with other crystalline forms of -{[(α-isobutanoyloxyethoxy)carbonyl]aminomethyl}-1-cyclohexane acetic acid.

5.6 Dosages

A crystalline form of 1-{[(α-isobutanoyloxyethoxy)carbonyl]aminomethyl}-1-cyclohexane acetic acid and/or pharmaceutical compositions thereof, will generally be used in an amount effective to achieve the intended purpose. For use to treat or prevent diseases or disorders such as epilepsy, pain (especially, neuropathic pain and muscular and skeletal pain), depression, anxiety, psychosis, faintness attacks, hypokinesia, cranial disorders, neurodegenerative disorders, panic, inflammatory disease (i.e., arthritis), insomnia, gastrointestinal disorders, hot flashes, restless legs syndrome, urinary incontinence or ethanol withdrawal syndrome the crystalline forms of 1-{[(α-isobutanoyloxyethoxy)carbonyl]aminomethyl}-1-cyclohexane acetic acid and/or pharmaceutical compositions thereof are administered or applied in a therapeutically effective amount.

The amount of a crystalline form of 1-{[(α-isobutanoyloxyethoxy)carbonyl]aminomethyl}-1-cyclohexane acetic acid and/or pharmaceutical compositions thereof that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a crystalline forms of 1-{[(α-isobutanoyloxyethoxy)carbonyl]aminomethyl}-1-cyclohexane acetic acid and/or pharmaceutical compositions thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiments, the crystalline forms of 1-{[(α-isobutanoyloxyethoxy)carbonyl] aminomethyl}-1-cyclohexane acetic acid and/or pharmaceutical compositions thereof are delivered by oral sustained release administration. Preferably, in these embodiments, the crystalline forms of 1-{[(α-isobutanoyloxyethoxy)carbonyl] aminomethyl}-1-cyclohexane acetic acid and/or pharmaceutical compositions thereof are administered twice per day (more preferably, once per day). Dosing may be repeated intermittently, may be provided alone or in combination with other drugs and may continue as long as required for effective treatment of the disease state or disorder.

In some embodiments, the dose of the crystalline forms of 1-{[(α-isobutanoyloxyethoxy)carbonyl]aminomethyl}-1-cyclohexane acetic acid and/or pharmaceutical compositions thereof may be adjusted to provide between about 500 mg/day and about 7000 mg/day of prodrug (equivalent to about 260 mg/day and about 3600 mg/day of gabapentin). Dosage ranges may be readily determined by methods known to the skilled artisan.

The crystalline forms of 1-{[(α-isobutanoyloxyethoxy) carbonyl]aminomethyl}-1-cyclohexane acetic acid and/or pharmaceutical compositions thereof are preferably assayed in vitro and in vivo, for the desired therapeutic or prophylactic activity, prior to use in humans. Preferably, a therapeutically effective dose of a crystalline forms of 1-{[(α-isobutanoyloxyethoxy)carbonyl]aminomethyl}-1-cyclohexane acetic acid and/or pharmaceutical compositions thereof described herein will provide therapeutic benefit without causing substantial toxicity. Toxicity of crystalline forms of 1-{[(α-isobutanoyloxyethoxy)carbonyl]aminomethyl}-1-cyclohexane acetic acid and/or pharmaceutical compositions thereof may be determined using standard pharmaceutical procedures and may be readily ascertained by the skilled artisan. The dose ratio between toxic and therapeutic effect is the therapeutic index. The dosage of crystalline forms of 1-{[(α-isobutanoyloxyethoxy)carbonyl]aminomethyl}-1-cyclohexane acetic acid and/or pharmaceutical compositions thereof described herein will preferably be within a range of circulating concentrations that include an effective dose with little or no toxicity.

5.7 Combination Therapy

In certain embodiments, crystalline forms of 1-{[(α-isobutanoyloxyethoxy)carbonyl]aminomethyl}-1-cyclohexane acetic acid and/or pharmaceutical compositions thereof can be used in combination therapy with at least one other therapeutic agent. The crystalline forms of 1-{[(α-isobutanoyloxyethoxy)carbonyl]aminomethyl}-1-cyclohexane acetic acid and/or pharmaceutical compositions thereof and the other therapeutic agent can act additively or, more preferably, synergistically. In some embodiments, a pharmaceutical composition comprising a crystalline form of 1-{[(α-isobutanoyloxyethoxy)carbonyl]aminomethyl}-1-cyclohexane acetic acid is administered concurrently with the administration of another therapeutic agent, which can be part of the same pharmaceutical composition as the crystalline form of 1-{[(α-isobutanoyloxyethoxy)carbonyl]aminomethyl}-1-cyclohexane acetic acid or a different pharmaceutical composition. In other embodiments, a pharmaceutical composition comprising a crystalline form of 1-{[(α-isobutanoyloxyethoxy)carbonyl]aminomethyl}-1-cyclohexane acetic acid is administered prior or subsequent to administration of another therapeutic agent. For example, a crystalline form of I-{[(o-isobutanoyloxyethoxy)carbonyl] aminomethyl}-1-cyclohexane acetic acid may be administered in combination with an amorphous form of 1-{[(α-isobutanoyloxyethoxy)carbonyl]aminomethyl}-1-cyclohexane acetic acid, another crystalline form of 1-{[(α-isobutanoyloxyethoxy)carbonyl]aminomethyl}-1-cyclohexane acetic acid, gabapentin or pregabalin.

6. EXAMPLES

The following examples describe in detail the preparation of 1-{[(α-isobutanoyloxyethoxy)carbonyl]aminomethyl}-1- cyclohexane acetic acid and a crystalline form thereof. It will be apparent to those skilled in the art that many modifications, both to materials and methods, may be practiced without departing from the scope of the invention.

In the examples below, the following abbreviations have the following meanings. If an abbreviation is not defined, the generally accepted meaning applies.

Atm=atmosphere
Boc=tert-butyloxycarbonyl
Cbz=carbobenzyloxy
DCC=dicyclohexylcarbodiimide
DMAP=4-N,N-dimethylaminopyridine
DMF=N,N-dimethylformamide
DMSO=dimethylsulfoxide
Fmoc=9-fluorenylmethyloxycarbonyl
g=gram
h=hour
HPLC=high pressure liquid chromatography
L=liter
LC/MS=liquid chromatography/mass spectroscopy
M=molar
min=minute
mL=milliliter
mmol=millimoles
NHS=N-hydroxysuccinimide
THF=tetrahydrofuran
TFA=trifluoroacetic acid
TLC=thin layer chromatography
TMS=trimethylsilyl
μL=microliter
μM=micromolar
v/v=volume to volume

6.1 Example 1

1-{[(α-Isobutanoyloxyethoxy)carbonyl]aminomethyl}-1-Cyclohexane Acetic Acid via Trimethylsilyl Ester Intermediate Step A: 1-{[(α-Chloroethoxy)carbonyl]aminomethyl}-1-Cyclohexane Acetic Acid In a 5-liter, 3-neck, round bottom flask containing dichloromethane (1.6 L) is added gabapentin (120.4 g, 0.704 mol) followed by triethylamine (294 mL, 2.11 mol). Chlorotrimethylsilane (178 mL, 1.40 mol) is slowly added while maintaining the reaction temperature below 15° C. and the resulting suspension is stirred for 30 min. 1-Chloroethyl chloroformate (100 g, 0.704 mol) is then added slowly while maintaining the temperature below 15° C. After the addition is complete, additional triethylamine (88 mL, 0.63 mol) is added and the resulting suspension is stirred at room temperature for 30 min. The resulting silyl ester is converted via acidic work-up to the corresponding acid by washing the reaction mixture with water (2×1 L), followed by 1N HCl (2×2 L) then brine (2×500 mL). After drying over anhydrous sodium sulfate and removal of the solvent in vacuo, the crude product (190 g) is obtained as an orange oil and used in Step B without further purification. $^1$H NMR (CDCl$_3$, 400 MHz): δ 1.41-1.57 (m, 10H), 1.78 (d, 3H), 2.33 (s, 2H), 3.27 (d, 2H), 5.42 (br. s, 1H), 6.55 (q, 1H).

Step B: 1-{[(α-Isobutanoyloxyethoxy)carbonyl]aminomethyl}-1-Cyclohexane Acetic Acid To a 3-liter, 3-neck, round bottom flask is added isobutyric acid (254 g, 2.9 mol) followed by triethylamine (395 ml, 2.84 mol). The reaction mixture is cooled to room temperature and a solution of crude acid from the above reaction step (190 g, 0.69 mol) in dichloromethane (80 mL) is added in a controlled fashion while maintaining the temperature below 30° C. The resulting pale yellow solution is stirred overnight. The reaction mixture is then diluted with one volume of dichloromethane and washed with water (6×500 mL), aqueous potassium bicarbonate (3×500 mL), and brine (2×500 mL). After drying over anhydrous sodium sulfate, removal of the solvent in vacuo affords the crude product as a dark red oil (87 g). A portion (35 g) of this product is loaded onto an 800 g Biotage™ normal phase silica gel flash column and eluted with 40% diethyl ether in hexane (6 L), which after removal of the solvent in vacuo affords the product as a colorless oil (13.5 g). This is repeated with a second 35 g portion of crude product yielding a further 13.5 g of 1-{[(α-isobutanoyloxyethoxy)carbonyl]aminomethyl}-1-cyclohexane acetic acid. A sample of the product (25 g) is recrystallized by dissolution in heptane (325 mL) at 70° C., followed by slow cooling to room temperature. The white crystalline product (23 g) is isolated by filtration. Melting point: 63-64° C.

6.2 Example 2

1-{[(α-Isobutanoyloxyethoxy)carbonyl]aminomethyl}-1-Cyclohexane Acetic Acid via Allyl Ester Intermediate Step A: Allyl 1-Aminomethyl-1-Cyclohexane Acetate Hydrochloride A dry 3 L, three-neck, round-bottomed flash fitted with a magnetic stirring bar and a 500 mL pressure-equalizing addition funnel is flushed with nitrogen gas. The flask is charged with gabapentin (171 g, 1.0 mol) and allyl alcohol (1 L, 852 g, 14.6 mol) and the entire mixture is cooled to 0° C. in an ice-water bath. Thionyl chloride (225 mL, 360 g, 3.0 mol) is added dropwise over a period of 1 h to the stirred solution. The reaction mixture is allowed to stir at room temperature for 16 h, then is diluted with ethyl ether (2 L) and cooled to 0° C. while stirring. After several minutes white crystals form formed, which are were collected by filtration. The crude product is recrystallized from a 1/3 (v/v) mixture of ethanol and ethyl ether (2 L) to give the product as a white solid (220 g 88%). m.p.: 138-142° C. $^1$H NMR (CD$_3$OD, 400 MHz): δ 1.36-1.54 (m, 10H), 2.57 (s, 2H), 3.05 (s, 2H), 4.61 (d, J=6 Hz, 2H), 5.22 (dd, J$_1$=10.4 Hz, J$_2$=1.2 Hz, 1H), 5.33 (dd, J$_1$=17.2 Hz, J$_2$=1.4 Hz, 1H), 5.90-6.00 (m, 1H). MS (ESI) m/z 212.0 (M-Cl)$^+$.

Step B: Allyl 1-{[(α-Chloroethoxy)carbonyl]aminomethyl}-1-Cyclohexane Acetate

To a solution of the above hydrochloride salt (220 g, 0.89 mol) in dichloromethane (1 L) is slowly added 1-chloroethyl chloroformate (101.7 mL, 132.3 g, 0.92 mol). The reaction mixture is cooled to 0° C. and 4-methylmorpholine (205 mL, 188.9 g, 1.87 mol) is slowly added over a period of 1 h while maintaining a temperature of less than 10° C. The resulting turbid solution is stirred at room temperature for 1 h. Ethanol (150 mL) is added and the reaction mixture is stirred at room temperature for 1 h. The reaction mixture is then diluted with ether (2.5 L), washed with water (1 L) and brine (1 L). The organic phase was is dried over sodium sulfate and concentrated to give the title compound as a light yellow viscous liquid (282 g, 100%). $^1$H NMR (CDCl$_3$, 400 MHz): δ 1.35-1.58 (m, 10H), 1.78 (d, J=5.6 Hz, 3H), 2.32 (s, 2H), 3.22 (d, J=6.8 Hz, 2H), 4.57 (d, J=5.6 Hz, 2H), 5.25 (dd, J$_1$=10.4 Hz, J$_2$=1 Hz, 1H), 5.32 (dd, J$_1$=17.2 Hz, J$_2$=1.6 Hz, 1H), 5.52 (br, 1H, NH), 5.90-5.94 (m, 1H), 6.54 (q, J=5.6 Hz, 1H).

Step C: Allyl 1-{[(α-Isobutanoyloxyethoxy)carbonyl]aminomethyl}-1-Cyclohexane Acetate To a mixture of isobutyric acid (432 mL, 391.5 g, 4.4 mol) and 4-methylmorpholine (488 mL, 449 g, 4.4 mol) is added a solution of the chlorocarbamate from the previous step (282 g, 0.88 mol) in isobutyric acid (432 mL, 391.5 g, 4.4 mol). The addition occurs occurred at 0° C. over a period of 30 min. The resulting turbid solution is stirred at room temperature for 16 h. The reaction mixture is diluted with ether (2.5 L) and washed with water (3×500 mL) followed by 10% aqueous potassium bicarbonate (6×500 mL) then brine (500 mL). The organic phase is dried over sodium sulfate and concentrated to yield the title compound as a viscous liquid (328 g, 100%). $^1$H NMR (CDCl$_3$, 400 MHz): δ 1.15 (d, J=7.2 Hz, 6H), 1.35-1.58 (m, 10H), 2.31 (s, 2H), 2.51 (m, 1H), 3.19 (d, J=5.6 Hz, 2H), 4.56 (d, J=5.6 Hz, 2H), 5.24 (dd, J$_1$=10 Hz, J$_2$=1 Hz, 1H), 5.32 (dd, J$_1$=17 Hz, J$_2$=1.2 Hz, 1H), 5.35 (br, 1H), 5.84-5.94 (m, 1H), 6.78 (q, J=5.6 Hz, 1H). MS (ESI) m/z 392.24 (M+H)$^+$.

Step D: Deprotection of Allyl 1-{[(α-Isobutanoyloxyethoxy)carbonyl]-aminomethyl}-1-Cyclohexane Acetate To a stirred suspension of ammonium formate (112 g, 1.7 mol) in ethanol (500 mL) was is added the above allyl ester (328 g, 0.88 mol) together with 10% Pd/C (15 g) under a nitrogen atmosphere. After 6 h, the reaction mixture is worked-up by filtering off the catalyst. The catalyst is washed with ethanol (2×250 mL) and the filtrates are were combined and evaporated. The crude product is dissolved in ether (2 L) and the organic phase is washed with 2N HCl (2×2 L) to convert the ammonium salt into the acid form, followed by washing with water (1 L) and brine (1 L). The ether layer is dried over sodium sulfate and concentrated to give the crude product as a viscous liquid (240 g, 82%).

Step E: Crystallization of 1-{[(α-Isobutanoyloxyethoxy)carbonyl]-aminomethyl}-1-Cyclohexane Acetic Acid A 3 L round-bottom flask is equipped with a heating oil bath, a nitrogen inlet adapter, an internal thermometer, an overhead mechanical stirrer, and a reflux condenser. The flask is flushed with nitrogen and charged with a 1/10 (v/v) mixture of ethyl acetate/heptane (1.2 L) and the crude product from the preceding reaction (240 g). The flask is heated until the product dissolves dissolved, then cooled according to the following schedule:

| Entry | Time (min.) | Temp (° C.) (Internal temp) | Appearance | Remarks |
|---|---|---|---|---|
| 1 | 0 | 18.0 | Solid in solvent | Start heating oil bath |
| 2 | 10 | 48 | Turbid | Slow dissolution of product |
| 4 | 20 | 58 | Clear solution | Turn off oil bath |
| 5 | 25 | 60 | Clear solution | Maximum temp. reached |
| 6 | 45 | 43 | Turbid | Compound crystallizing |
| 7 | 60 | 36 | Milky solution | Seed with pure ref. material |
| 8 | 90 | 24 | Solid in solution | |

The flask is then cooled to 4° C. overnight with stirring (cooling improves the yield). The product is filtered and washed with heptane (2×100 mL), then is dried under reduced pressure (25 mm of Hg (0.033 atm)) at 30° C. for 18 h to yield 1-{[(α-isobutanoyloxyethoxy)carbonyl]aminomethyl}-1-cyclohexane acetic acid (185 g) as a white crystalline solid.

6.3 Example 3

X-Ray Powder Diffraction Analysis of Crystalline 1-{[(α-Isobutanoyloxyethoxy)carbonyl]aminomethyl}-1-Cyclohexane Acetic Acid X-ray powder diffractograms (XRPD's) of crystalline samples of 1-{[(α-isobutanoyloxyethoxy)carbonyl]aminomethyl}-1-cyclohexane acetic acid produced according to Examples 1 and 2 above are measured with a Bruker D8 Discover X-ray powder diffractometer using Cu Kα radiation. The instrument is equipped with parallel beam optics and a two-dimensional HI-STAR area detector. The tube voltage and amperage are were set to 40 kV and 40 mA, respectively. The collimated X-ray beam is reduced to a spot size of about 0.5 mm in diameter. The area detector is placed 15 cm from the center of the goniometer and the angular resolution is approximately 0.033°/pixel. The detector covers a range of 35° in 2-theta (2θ) within one frame. The angle between the X-ray beam and the horizontal sample plate is set to 4° and the center of the area detector is set to an angle of 18°. This geometry allows allowed the measurement of 2-theta from 4.5° to 39.5° within one frame. Typical averaging time is 3 minutes for each XRPD pattern collected. A corundum sample (NIST 1976) is used to calibrate the XRPD instrument. Both samples give equivalent diffractogram patterns, as illustrated in FIG. 1.

6.4 Example 4

Melting Point and Differential Scanning Calorimetry Analysis of Crystalline 1-{[(α-Isobutanoyloxyethoxy)carbonyl]aminomethyl}-1-Cyclohexane Acetic Acid Melting points of crystalline samples of 1-{[(α-isobutanoyloxyethoxy)carbonyl]aminomethyl}-1-cyclohexane acetic acid produced according to Examples 1 and 2 above are were measured using an Electrothermal 9200 melting point apparatus and are determined to be 63-64° C.

Differential scanning calorimetry (DSC) analysis of crystalline samples of 1-{[(α-isobutanoyloxyethoxy)carbonyl]aminomethyl}-1-cyclohexane acetic acid produced according to Examples 1 and 2 above are measured using a Perkin Elmer Series 7 instrument, scanning from 25° C. to 250° C. at a scan rate of 5° C./minute. A test portion of the sample is placed in an aluminum pan and the cap crimped to eliminate any visible seam between the cap and the pan. An empty pan is prepared in the same manner as a blank. The pans are were placed in the Differential Scanning Calorimeter. The material is run at the appropriate temperature program (Equilibration at Initial Temp, Isothermal, Ramp Rate, Final Temp) to produce the thermogram shown in FIG. 2. DSC analysis show an endothermic transition with an onset temperature of 58.3° C. and a ΔH of 72.39 J/g. At the peak endotherm of 63-64° C. the sample visibly melts melted.

6.5 Example 5

{[(1-Isobutanoyloxyethoxy)carbonyl]aminomethyl}-1-Cyclohexane Acetic Acid

To a solution of gabapentin (6.8 g, 0.04 mole) in water (40 mL) is added a solution of [(1-isobutanoyloxyethoxy)carbonyloxy]succinimide (10 g, 0.036 mol) in acetonitrile (40 mL) over a period of 30 minutes. The reaction is stirred at ambient temperature for 3 hours. The reaction mixture is diluted with methyl tert-butyl ether (200 mL), washed with water (2×100 mL) and brine (50 mL). The organic phase is separated, dried over anhydrous sodium sulfate, filtered, and concentrated in vacuo to afford the title compound as a white solid (12 g, quantitative).

Crystallization: The solid compound (12 g) is suspended in methylcyclohexane: methyl tert-butyl ether 10:1 (60 mL). The suspension is slowly heated up to 50° C. over a period of 30 minutes. The clear solution is then allowed to cool to room temperature. The turbid mixture is seeded with 5 mg of the title compound in crystalline form. The mixture is further cooled to 0-4° C. for 2 hours. The solid product is filtered and washed with methylcyclohexane (2×10 mL) to yield the title compound as a white crystalline solid (10 g, 83% yield). The crystalline solid material has had a melting point of about 64-66° C. as measured by open capillary melting point determination.

Finally, it should be noted that there are alternative ways of implementing the present invention. Accordingly, the present embodiments are to be considered as illustrative and not restrictive, and the invention is not to be limited to the details given herein, but may be modified within the scope and equivalents of any claim(s) issuing herefrom. All publications and patents cited herein are incorporated by reference in their entirety.

The invention claimed is:

1. Crystalline 1-{[(α-isobutanoyloxyethoxy)carbonyl]aminomethyl}-1-cyclohexane acetic acid having characteristic absorption peaks at 7.0°±0.3°, 8.2°±0.3°, 10.5°±0.3°, 12.8°±0.3°, 14.9°±0.3°, and 16.4°±0.3° in an X-ray powder diffractogram using Cu Kα radiation.

2. Crystalline 1-{[(α-isobutanoyloxyethoxy)carbonyl]aminomethyl}-1-cyclohexane acetic acid having an X-ray powder diffractogram using Cu Kα radiation illustrated in FIG. 1.

3. Crystalline 1-{[(α-isobutanoyloxyethoxy)carbonyl]aminomethyl}-1-cyclohexane acetic acid having a melting point range of between about 63° C. and about 64° C. as determined by differential scanning calorimetry at a scan rate of 5° C./minute.

4. Crystalline 1-{[(α-isobutanoyloxyethoxy)carbonyl]aminomethyl}-1-cyclohexane acetic acid having the characteristic absorption peaks recited in claim 1 and having a characteristic absorption peak at 17.9°±0.3° in the X-ray powder diffractogram using Cu Kα radiation.

5. Crystalline 1-{[(α-isobutanoyloxyethoxy)carbonyl]aminomethyl}-1-cyclohexane acetic acid having the characteristic absorption peaks recited in claim 1 and having a characteristic absorption peak at 18.1°±0.3° in the X-ray powder diffractogram using Cu Kα radiation.

6. Crystalline 1-{[(α-isobutanoyloxyethoxy)carbonyl]aminomethyl}-1-cyclohexane acetic acid having the characteristic absorption peaks recited in claim 1 and having a characteristic absorption peak at 18.9°±0.3° in the X-ray powder diffractogram using Cu Kα radiation.

7. Crystalline 1-{[(α-isobutanoyloxyethoxy)carbonyl]aminomethyl}-1-cyclohexane acetic acid having the characteristic absorption peaks recited in claim 1 and having a characteristic absorption peak at 20.9°±0.3° in the X-ray powder diffractogram using Cu Kα radiation.

8. Crystalline 1-{[(α-isobutanoyloxyethoxy)carbonyl]aminomethyl}-1-cyclohexane acetic acid having the characteristic absorption peaks recited in claim 1 and having a characteristic absorption peak at 23.3°±0.3° in the X-ray powder diffractogram using Cu Kα radiation.

9. Crystalline 1-{[(α-isobutanoyloxyethoxy)carbonyl]aminomethyl}-1-cyclohexane acetic acid having the characteristic absorption peaks recited in claim 1 and having a characteristic absorption peak at 25.3°±0.3° in the X-ray powder diffractogram using Cu Kα radiation.

10. Crystalline 1-{[(α-isobutanoyloxyethoxy)carbonyl]aminomethyl}-1-cyclohexane acetic acid having the characteristic absorption peaks recited in claim 1 and having a characteristic absorption peak at 26.6°±0.3° in the X-ray powder diffractogram using Cu Kα radiation.

11. Crystalline 1-{[(α-isobutanoyloxyethoxy)carbonyl]aminomethyl}-1-cyclohexane acetic acid having the characteristic absorption peaks recited in claim 1 and having characteristic absorption peaks at 17.9°±0.3°, 18.9°±0.3°, 20.9°±0.3°, 23.3°±0.3°, 25.3°±0.3° and 26.6°±0.3° in the X-ray powder diffractogram using Cu Kα radiation.

12. Crystalline 1-{[(α-isobutanoyloxyethoxy)carbonyl]aminomethyl}-1-cyclohexane acetic acid having the characteristic absorption peaks recited in claim 1 and having characteristic absorption peaks at 18.1°±0.3°, 18.9°±0.3°, 20.9°±0.3°, 23.3°±0.3°, 25.3°±0.3° and 26.6°±0.3° in the X-ray powder diffractogram using Cu Kα radiation.

13. Crystalline 1-{[(α-isobutanoyloxyethoxy)carbonyl]aminomethyl}-1-cyclohexane acetic acid having the characteristic absorption peaks recited in claim 1 and having characteristic absorption peaks at 17.9°±0.3°, 18.1°±0.3°, 18.9°±0.3°, 20.9°±0.3°, 23.3°±0.3°, 25.3°±0.3° and 26.6°±0.3° in the X-ray powder diffractogram using Cu Kα radiation.

14. Crystalline 1-{[(α-isobutanoyloxyethoxy)carbonyl]aminomethyl}-1-cyclohexane acetic acid according to claim 1, having a melting point range of between about 63° C. and about 64° C. as determined by differential scanning calorimetry at a scan rate of 5° C./minute.

15. Crystalline 1-{[(α-isobutanoyloxyethoxy)carbonyl]aminomethyl}-1-cyclohexane acetic acid according to claim 11, having a melting point range of between about 63° C. and about 64° C. as determined by differential scanning calorimetry at a scan rate of 5° C./minute.

16. Crystalline 1-{[(α-isobutanoyloxyethoxy)carbonyl]aminomethyl}-1-cyclohexane acetic acid according to claim 11, having a melting point range of between about 63° C. and about 64° C. as determined by differential scanning calorimetry at a scan rate of 5° C./minute.

17. Crystalline 1-{[(α-isobutanoyloxyethoxy)carbonyl]aminomethyl}-1-cyclohexane acetic acid according to claim 13, having a melting point range of between about 63° C. and about 64° C. as determined by differential scanning calorimetry at a scan rate of 5° C./minute.

* * * * *